United States Patent
Deng

(10) Patent No.: US 10,575,425 B1
(45) Date of Patent: Feb. 25, 2020

(54) WATERPROOF HOUSING FOR WEARABLE DEVICE

(71) Applicant: SHENZHEN XIWXI TECHNOLOGY CO., LTD, Shenzhen (CN)

(72) Inventor: Xiuhong Deng, Longhui (CN)

( * ) Notice: Subject to any disclaimer, the term of this patent is extended or adjusted under 35 U.S.C. 154(b) by 0 days.

(21) Appl. No.: 16/436,975

(22) Filed: Jun. 11, 2019

(51) Int. Cl.
| | |
|---|---|
| *H05K 5/06* | (2006.01) |
| *A61B 5/00* | (2006.01) |
| *H05K 5/03* | (2006.01) |
| *H05K 5/00* | (2006.01) |
| *H05K 5/02* | (2006.01) |

(52) U.S. Cl.
CPC ............. *H05K 5/069* (2013.01); *A61B 5/681* (2013.01); *H05K 5/0017* (2013.01); *H05K 5/0086* (2013.01); *H05K 5/0217* (2013.01); *H05K 5/03* (2013.01); *H05K 5/061* (2013.01)

(58) Field of Classification Search
CPC combination set(s) only.
See application file for complete search history.

(56) References Cited

U.S. PATENT DOCUMENTS

| | | | | |
|---|---|---|---|---|
| 8,773,847 | B2 * | 7/2014 | Byun | H04B 1/385 361/679.03 |
| 9,391,307 | B2 * | 7/2016 | Ishibashi | H01M 2/1066 |
| 9,639,119 | B2 * | 5/2017 | Seok | A61B 5/681 |
| 9,992,893 | B2 * | 6/2018 | Choi | H05K 5/03 |
| 10,285,643 | B2 * | 5/2019 | Perkins | A61B 5/0059 |
| 2015/0137731 | A1 * | 5/2015 | Kim | H02J 7/355 320/101 |
| 2015/0359436 | A1 * | 12/2015 | Shim | A61B 5/7278 600/301 |
| 2016/0022210 | A1 * | 1/2016 | Nuovo | A61B 5/681 600/301 |
| 2016/0309604 | A1 * | 10/2016 | Steijner | E06B 7/22 |
| 2017/0011210 | A1 * | 1/2017 | Cheong | A61B 5/0022 |
| 2018/0063981 | A1 * | 3/2018 | Park | H05K 5/069 |
| 2019/0328325 | A1 * | 10/2019 | Parara | G16H 40/67 |

* cited by examiner

*Primary Examiner* — Lisa Lea-Edmonds
(74) *Attorney, Agent, or Firm* — HYIP

(57) ABSTRACT

The present disclosure provides a waterproof housing for wearable device, including a housing. The housing includes a first surface and a second surface opposite to the first surface. A first opening formed by an inward depression of the first surface, a second opening formed by an inward depression of the second surface. A first transparent layer is sealed at the first opening so as to expose the screen display of the wearable device. The second transparent layer is sealed at the second opening so as to realize the sensor detection of the wearable device. The present disclosure can better protect wearable device without affecting the health data detection of users by wearable device.

15 Claims, 6 Drawing Sheets

WATERPROOF HOUSING FOR WEARABLE DEVICE

TECHNICAL FILED

The present disclosure relates to a terminal device housing, in particular to a waterproof housing for wearable device.

BACKGROUND

Generally, a wearable device is usually not equipped with a waterproof housings which fits the wearable device, and the waterproof function is rely on the wearable device itself. Although the wearable device itself has a certain waterproof function, the wearable device is easy to be scratched or broken due to without other protection, even at some time, moisture can also enter the device and damage the device.

SUMMARY OF THE DISCLOSURE

In view of this, it is necessary to provide a waterproof housing for a wearable device that can better protect the wearable device without affecting the health data detection of the user by the wearable device.

The present disclosure provides a waterproof housing for a wearable device, including a housing, the housing includes a first surface and a second surface opposite to the first surface. A first opening formed by an inward depression of the first surface, a second opening formed by an inward depression of the second surface. A first transparent layer is sealed at the first opening so as to expose the screen display of the wearable device, the second transparent layer is sealed at the second opening so as to realize sensor detection of the wearable device.

Further, the housing includes a housing body and a cover being sealingly connected to the housing body.

Further, the housing body is made of hard rubber, and the cover is made of soft rubber.

Further, the first opening is set on the housing body, and the second opening is set on the cover.

Further, the cover is formed with a first annular groove and/or a first annular hook, and the housing body is formed with a second annular hook corresponding to the first annular groove and/or a second annular groove corresponding to the first annular hook. The first annular groove is connected to the second annular hook, the first annular hook is connected to the second annular groove.

Further, an upper surface of the cover is recessed downwardly at first and then gradually recessed outwardly, so that the first annular groove and the first annular hook are formed on the cover; an lower surface of the housing body is recessed upwardly at first and then gradually recessed inwardly, so that the second annular groove and the second annular hook are formed on the housing body.

Further, the second transparent layer is integrally formed with the housing.

Further, an edge of the second transparent layer is embedded within the housing.

Further, the housing is provided with an adjustment button, and a position of the adjustment button corresponds to a position of a function button on the wearable device.

Further, the adjustment button is sealingly connected to the housing by a waterproof sealing ring.

Further, the waterproof sealing ring includes a first collar and a second collar extending outwardly from an outer periphery of the first collar; the axial length of the first collar is longer than that of the second collar, an inner surface of the first collar is in contact with the outer peripheral surface of the adjustment button, and the outer peripheral surface of the second collar is in contact with the housing.

Further, the second collar is located in a middle of the first collar.

Further, the adjustment button comprises a pressing button and a screwing button; the pressing button matches with one function button in a pressing manner, the screwing button matches with another function button in a rotating manner.

Further, the screwing button comprises an adjusting portion which is at least partially exposed and a rubber portion connected to the adjusting portion; the rubber portion is in frictional contact with the function button.

Further, the housing is provided with a microphone hole, a position of the microphone hole corresponds to a position of a microphone on the wearable device.

Compared with the prior art, the present disclosure has the beneficial effects that the present disclosure worked as a protective housing of the wearable device can not only improves the protective effect of the wearable device, but also provides with a second transparent layer, which will not hinder the detection of human health data by sensors on wearable devices.

Figure 1:
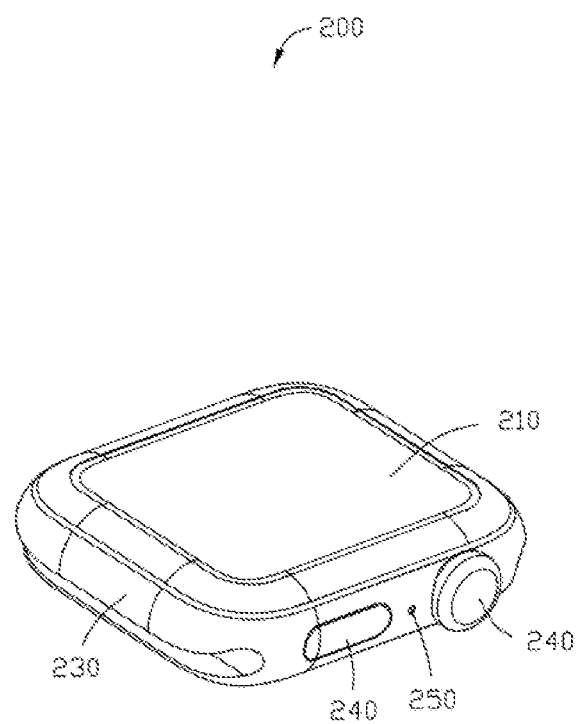
FIG. 1 is a schematic structural view of a first direction of a wearable device to which the present disclosure is applied.

The present disclosure will be further illustrated by the following detailed description in conjunction with the accompanying drawings.

DETAILED DESCRIPTION OF THE EMBODIMENTS

The technical solutions in the embodiments of the present disclosure are clearly and completely described in the following with reference to the accompanying drawings in the embodiments of the present disclosure. It is obvious that the described embodiments are only a part of the embodiments of the present disclosure, but not all embodiments. All other embodiments obtained by those skilled in the art based on the embodiments of the present disclosure without creative efforts are within the scope of the present disclosure. It is to be understood that the accompanying drawings are only for providing reference and description use, not intended to limit the present disclosure. The connection relationships shown in the drawings are for convenience of clarity and do not limit the connection.

Figure 2:
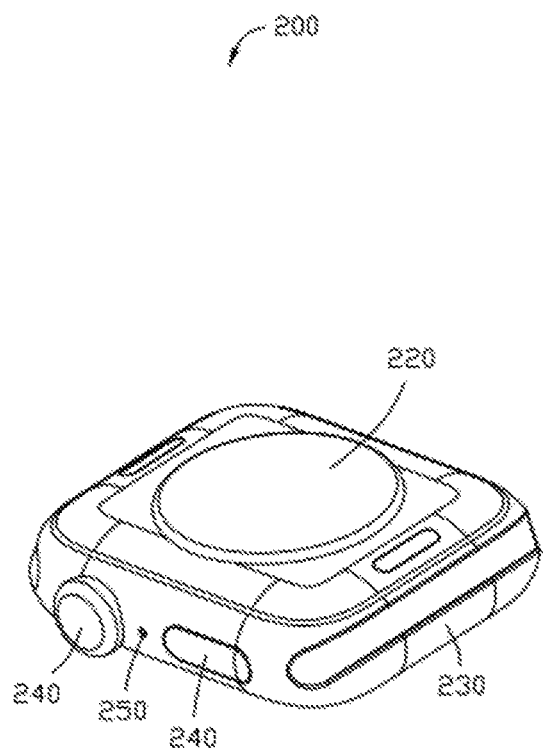
FIG. 2 is a schematic structural view of a second direction of a wearable device to which the present disclosure is applied.

The present disclosure provides a waterproof housing 100 for protecting the wearable device 200. As shown in FIG. 1 and FIG. 2, wherein the wearable device 200 includes a main body 230 and a screen 210 setting on a top surface of the main body 230. Through the screen 210 can display various information such as time and/or number of steps and/or heart rate and/or pulse, etc. As shown in FIG. 2, at least one sensor 220 is set under the main body 230, and the sensor 220 can be used to detect health information of a user, such as heart rate, pulse and the like. The side of the main body 230 may also be provided with one or more function buttons 240 and a microphone 250 by which the function of the main body 230 can be adjusted.

Figure 3:
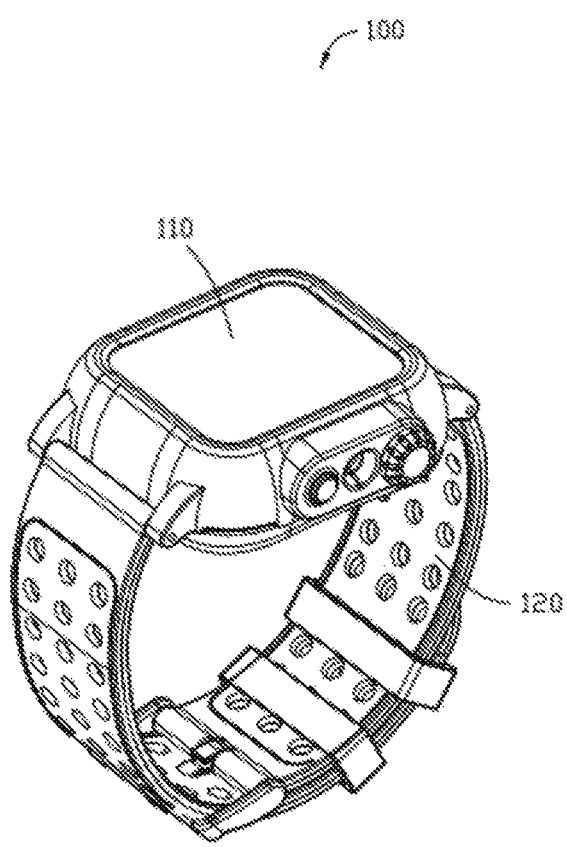
FIG. 3 is a schematic view showing the structure of the waterproof housing of the present disclosure.

As shown in FIG. 3, the waterproof housing 100 includes a housing 110 and a watchband 120 connected to the housing.

Figure 4:
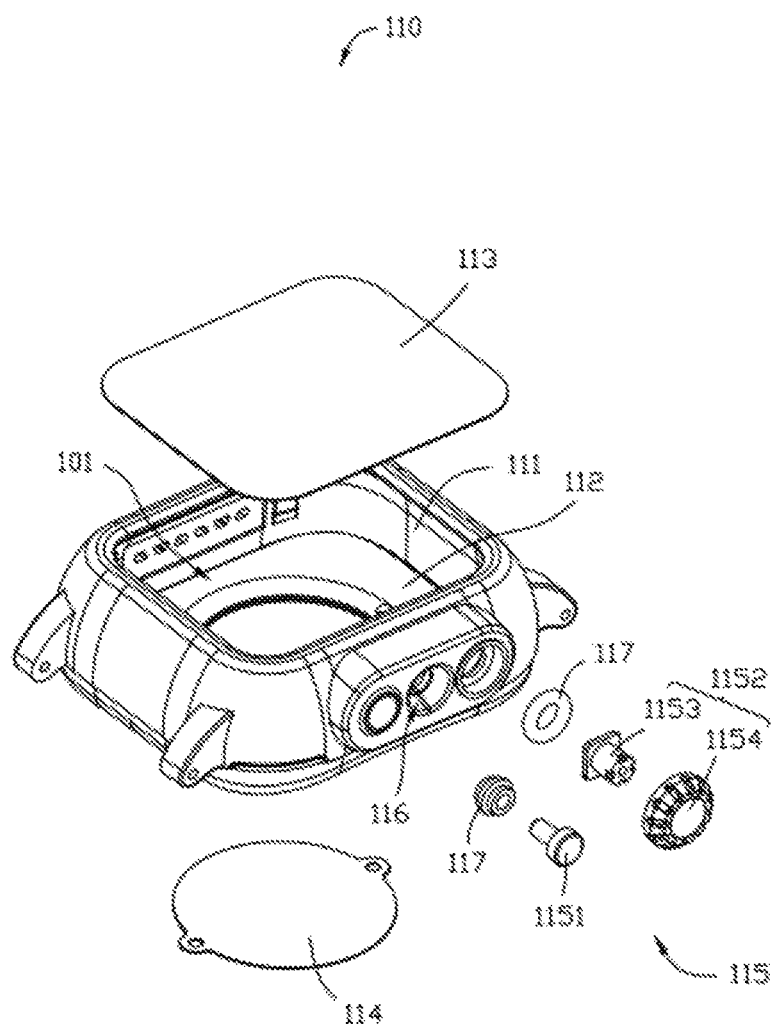
FIG. 4 is an exploded view of the present disclosure.

As shown in FIG. 4, the housing 110 may include a housing body 111 and a cover body 112. The housing body 111 and the cover body 112 are sealingly connected to form the housing 110. The housing 110 has a cavity 101 for receiving the wearable device, when in use, the wearable device 200 is housed in the cavity 101 for protection.

Figure 5:
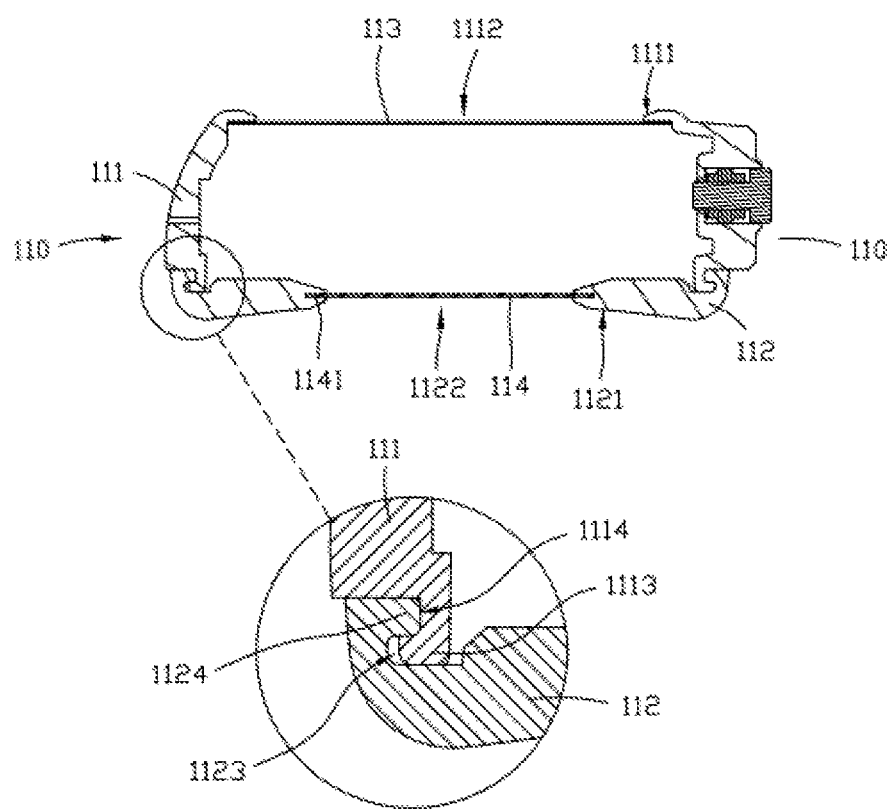
FIG. 5 is a cross-sectional view of the present disclosure.

As shown in FIG. 5, the housing body 111 includes a first surface 1111. The first surface 1111 is on the upper side of the housing 110. The cover 112 is provided with a second surface 1121. The second surface 1121 is on the lower side of the housing 110 and faced to the first surface 1111. The first surface 1111 is recessed inwardly to form a first opening 1112. The second surface 1121 is recessed inwardly to form a second opening 1122. The first opening 1112 is sealed with a first transparent layer 113. The second opening 1122 is sealed with a second transparent layer 114. Thus, the user can see the screen 210 of the wearable device 200 through the first transparent layer 113, and the detection wave of the sensor 220 can pass through the second transparent layer 114 to reach the human skin, and then return from the second transparent layer 114, so as to analyze and obtain various health data.

In this embodiment, the housing body 111 is made of hard rubber, and the cover 112 is made of soft rubber. Thus, the cover 112 is connected to the housing body 111 to achieve a sealing effect. It is not necessary to separately provide a waterproof sealing ring, which simplifies the structure and installation process and is more convenient for installation.

As shown in FIG. 5, the cover 112 is formed with a first annular groove 1123 and/or a first annular hook 1124, and the housing body 111 is formed with a second annular hook 1113 corresponding to the first annular groove 1123 and/or a second annular groove 1114 corresponding to the first annular hook 1124, the first annular groove 1123 is connected to the second annular hook 1113, the first annular hook 1124 is connected to the second annular groove 1114, such that the cover 112 and the housing body 111 are sealingly connected.

In this embodiment, an upper surface of the cover 112 is recessed downwardly at first and then gradually recessed outwardly, so that the first annular groove 1123 and the first annular hook 1124 are formed on the cover 112. An lower surface of the housing body 111 is recessed upwardly at first and then gradually recessed inwardly, so that the second annular groove 1114 and the second annular hook 1113 are formed on the housing body 111.

In this embodiment, in order to improve the sealing performance of the second transparent layer 114 and the housing 110, the second transparent layer 114 is integrally formed with the housing 110. In order to further improve the sealing performance and firmness of the second transparent layer 114 and the housing 110, and the edge 1141 of the second transparent layer 114 is embedded in the housing 110.

In this embodiment, referring back to FIG. 4, the housing 110 is provided with an adjustment button 115 and a microphone hole 116. The number of the adjustment buttons 115 is the same as the number of the function buttons 240 of the wearable device 200. The position of the adjustment buttons 115 corresponds to the position of the function button 240 on the wearable device 200, the position of the microphone hole 116 corresponds to the position of the microphone 250 on the wearable device 200.

The adjustment button 115 may include a pressing button 1151 and a screwing button 1152. The pressing button 1151 matches with one function button 240 in a pressing manner. By pressing the pressing button 1151 to press the function button 240, so that the wearable device 200 can be adjusted. The screwing button 1152 matches with another function button 240 in a rotating manner. By rotating the screwing button 1152 to drive the rotation of the function button 240, so that the wearable device 200 can be adjusted. Specifically, the screwing button 1152 includes an adjusting portion 1153 which is at least partially exposed and a rubber portion 1154 connected to the adjusting portion 1153. The rubber portion 1154 is in frictional contact with the function button 240.

The adjustment button 115 is sealingly connected to the housing through a waterproof sealing ring 117. Surely, the adjustment button may also be integrally formed with the housing and fixed to the housing.

Figure 6:
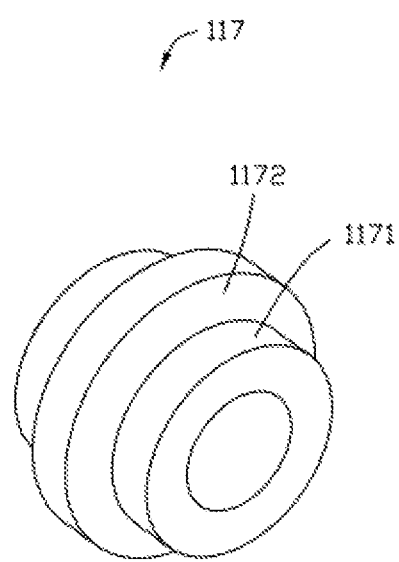
FIG. 6 is a schematic structural view of a waterproof sealing ring according to an embodiment of the present disclosure.

As shown in FIG. 6, the waterproof sealing ring 117 includes a first collar 1171 and a second collar 1172 extending outwardly from an outer periphery of the first collar 1171. The axial length of the first collar 1171 is longer than that of the second collar 1172, an inner surface of the first collar 1171 is in contact with the outer peripheral surface of the adjustment button 115, and the outer peripheral surface of the second collar 1172 is in contact with the housing 110. Specifically, the second collar 1172 is located in a middle of the first collar 1171. Particularly, because the axial length of the first collar 1171 is longer than that of the second collar 1172, the contact area between the second collar 1172 and the housing 110 is smaller than the contact area between the first collar 1171 and the adjustment button 115, the sealing effect between the first collar 1171 and the adjustment button 115 is enhanced, not only a good seal can be achieved, but also the resistance of the waterproof sealing ring 117 to the movement can be reduced if the adjustment button 115 telescopically moves relative to the housing 110, the second collar 1172 has a small contact area and is more easily deformed, thereby facilitating the pressing of the adjustment button 115.

The above is only the preferred embodiment of the present disclosure, and is not intended to limit the present disclosure. Any modifications, equivalent substitutions and improvements made within the spirit and principles of the present disclosure should be within the scope of the present disclosure.

What is claimed is:

1. A waterproof housing for a wearable device, comprising a housing, wherein the housing comprises a first surface and a second surface opposite to the first surface; a first opening formed by an inward depression of the first surface, a second opening formed by an inward depression of the second surface; a first transparent layer is sealed at the first opening so as to expose the screen display of the wearable device, the second transparent layer is sealed at the second opening so as to realize sensor detection of the wearable device.

2. The waterproof housing of claim 1 wherein the housing comprises a housing body and a cover being sealingly connected to the housing body.

3. The waterproof housing of claim 2, wherein the housing body is made of hard rubber, and the cover is made of soft rubber.

4. The waterproof housing of claim 3, wherein the first opening is set on the housing body, and the second opening is set on the cover.

5. The waterproof housing of claim 3, wherein the cover is formed with a first annular groove and/or a first annular hook, and the housing body is formed with a second annular hook corresponding to the first annular groove and/or a second annular groove corresponding to the first annular hook, the first annular groove is connected to the second annular hook, the first annular hook is connected to the second annular groove.

6. The waterproof housing of claim 5, wherein an upper surface of the cover is recessed downwardly at first and then gradually recessed outwardly, so that the first annular groove and the first annular hook are formed on the cover; an lower surface of the housing body is recessed upwardly at first and then gradually recessed inwardly, so that the second annular groove and the second annular hook are formed on the housing body.

7. The waterproof housing of claim 1, wherein the second transparent layer is integrally formed with the housing.

8. The waterproof housing of claim 7, wherein an edge of the second transparent layer is embedded within the housing.

9. The waterproof housing of claim 1, wherein the housing is provided with an adjustment button, and a position of the adjustment button corresponds to a position of a function button on the wearable device.

10. The waterproof housing of claim 9, wherein the adjustment button is sealingly connected to the housing by a waterproof sealing ring.

11. The waterproof housing of claim 10, wherein the waterproof sealing ring comprises a first collar and a second collar extending outwardly from an outer periphery of the first collar; the axial length of the first collar is longer than that of the second collar, an inner surface of the first collar is in contact with the outer peripheral surface of the adjustment button, and the outer peripheral surface of the second collar is in contact with the housing.

12. The waterproof housing of claim 11, wherein the second collar is located in a middle of the first collar.

13. The waterproof housing of claim 9, wherein the adjustment button comprises a pressing button and a screwing button; the pressing button matches with one function button in a pressing manner, the screwing button matches with another function button in a rotating manner.

14. The waterproof housing of claim 13, wherein the screwing button comprises an adjusting portion which is at least partially exposed and a rubber portion connected to the adjusting portion; the rubber portion is in frictional contact with the function button.

15. The waterproof housing of claim 1, wherein the housing is provided with a microphone hole, a position of the microphone hole corresponds to a position of a microphone on the wearable device.

* * * * *